(12) United States Patent
Hush et al.

(10) Patent No.: US 12,718,870 B2
(45) **Date of Patent: *Aug. 25, 2026**

(54) MEMORY DEVICE FOR WAFER-ON-WAFER FORMED MEMORY AND LOGIC

(71) Applicant: Micron Technology, Inc., Boise, ID (US)

(72) Inventors: Glen E. Hush, Boise, ID (US); Sean S. Eilert, Penryn, CA (US); Aliasger T. Zaidy, Seattle, WA (US); Kunal R. Parekh, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 138 days.

This patent is subject to a terminal disclaimer.

(21) Appl. No.: 18/820,840

(22) Filed: Aug. 30, 2024

(65) Prior Publication Data

US 2024/0420757 A1 Dec. 19, 2024

Related U.S. Application Data

(63) Continuation of application No. 17/712,935, filed on Apr. 4, 2022, now Pat. No. 12,112,792.

(Continued)

(51) Int. Cl.
*H01L 23/00* (2006.01)
*G06F 3/06* (2006.01)

(Continued)

(52) U.S. Cl.
CPC ........ *G11C 11/4093* (2013.01); *G06F 3/0656* (2013.01); *G06F 13/1673* (2013.01); *G06F 13/28* (2013.01); *G11C 7/08* (2013.01); *G11C 7/1039* (2013.01); *G11C 11/4087* (2013.01); *G11C 11/4091* (2013.01); *G11C 11/4096* (2013.01); *G16B 30/00* (2019.02); *G16B 50/10* (2019.02); *H10P 54/00* (2026.01); *H10P 74/203* (2026.01); *H10W 72/50* (2026.01); *H10W 72/90* (2026.01); *H10W 90/00* (2026.01); *H10W 99/00* (2026.01); *G06F 2213/28* (2013.01);

(Continued)

(58) Field of Classification Search

CPC . G11C 11/4093; G11C 7/08; G11C 117/1039; G11C 11/4079; G11C 11/4091; G11C 11/4096; G06F 3/0656; G06F 13/28

See application file for complete search history.

(56) References Cited

U.S. PATENT DOCUMENTS 10,665,580 B1 5/2020 Hosoda et al.
11,430,766 B2 8/2022 Liu et al.

(Continued)

*Primary Examiner* — Min Huang

(74) *Attorney, Agent, or Firm* — Brooks, Cameron & Huebsch, PLLC

(57) ABSTRACT

A memory device includes an array of memory cells configured on a die or chip and coupled to sense lines and access lines of the die or chip and a respective sense amplifier configured on the die or chip coupled to each of the sense lines. Each of a plurality of subsets of the sense lines is coupled to a respective local input/output (I/O) line on the die or chip for communication of data on the die or chip and a respective transceiver associated with the respective local I/O line, the respective transceiver configured to enable communication of the data to one or more device off the die or chip.

20 Claims, 13 Drawing Sheets

Related U.S. Application Data

(60) Provisional application No. 63/231,660, filed on Aug. 10, 2021.

(51) Int. Cl.

| | |
|---|---|
| ***G06F 13/16*** | (2006.01) |
| ***G06F 13/28*** | (2006.01) |
| ***G11C 7/08*** | (2006.01) |
| ***G11C 7/10*** | (2006.01) |
| ***G11C 11/408*** | (2006.01) |
| ***G11C 11/4091*** | (2006.01) |
| ***G11C 11/4093*** | (2006.01) |
| ***G11C 11/4096*** | (2006.01) |
| ***G16B 30/00*** | (2019.01) |
| ***G16B 50/10*** | (2019.01) |
| ***H10P 54/00*** | (2026.01) |
| ***H10P 74/20*** | (2026.01) |
| ***H10W 72/50*** | (2026.01) |
| ***H10W 72/90*** | (2026.01) |
| ***H10W 90/00*** | (2026.01) |
| ***H10W 99/00*** | (2026.01) |
| *H10W 72/00* | (2026.01) |
| *H10W 72/20* | (2026.01) |
| *H10W 80/00* | (2026.01) |
| *H10W 90/20* | (2026.01) |
| *H10W 90/26* | (2026.01) |

(52) U.S. Cl.

CPC ...... *H10W 72/01* (2026.01); *H10W 72/07252* (2026.01); *H10W 72/20* (2026.01); *H10W 72/221* (2026.01); *H10W 80/312* (2026.01); *H10W 80/327* (2026.01); *H10W 80/721* (2026.01); *H10W 90/20* (2026.01); *H10W 90/26* (2026.01); *H10W 90/288* (2026.01); *H10W 90/297* (2026.01); *H10W 90/721* (2026.01); *H10W 90/724* (2026.01); *H10W 90/751* (2026.01); *H10W 90/752* (2026.01); *H10W 90/792* (2026.01)

(56) References Cited

U.S. PATENT DOCUMENTS

| | | | | |
|---|---|---|---|---|
| 12,112,792 | B2* | 10/2024 | Hush | G06F 13/28 |
| 2003/0126314 | A1 | 7/2003 | Litt | |
| 2016/0172028 | A1 | 6/2016 | Park et al. | |
| 2019/0043836 | A1 | 2/2019 | Fastow et al. | |
| 2020/0135720 | A1 | 4/2020 | Brewer | |
| 2020/0243486 | A1* | 7/2020 | Quader | H10W 90/00 |
| 2021/0118488 | A1* | 4/2021 | Kim | G06N 3/063 |
| 2021/0225430 | A1* | 7/2021 | O | G06F 13/1668 |
| 2022/0230695 | A1 | 7/2022 | Park et al. | |
| 2023/0048855 | A1 | 2/2023 | Eilert et al. | |

* cited by examiner 228
256
32
230
238
232
234
236
32 LOCAL IO LINES (1024 SENSE AMP BITS)
GLOBAL IO LINES (256 BITS TOTAL)

MEMORY DEVICE FOR WAFER-ON-WAFER FORMED MEMORY AND LOGIC

CROSS-REFERENCE TO RELATED APPLICATIONS

This application is a Continuation of U.S. application Ser. No. 17/712,935, filed Apr. 4, 2022, which claims the benefit of U.S. Provisional Application 63,231,660, filed Aug. 10, 2021, which is incorporated by reference.

TECHNICAL FIELD

The present disclosure relates generally to memory, and more particularly to apparatuses and methods associated with a memory device for wafer-on-wafer formed memory and logic.

BACKGROUND

Memory devices are typically provided as internal, semiconductor, integrated circuits in computers or other electronic devices. There are many different types of memory including volatile and non-volatile memory. Volatile memory can require power to maintain its data and includes random-access memory (RAM), dynamic random access memory (DRAM), and synchronous dynamic random access memory (SDRAM), among others. Non-volatile memory can provide persistent data by retaining stored data when not powered and can include NAND flash memory, NOR flash memory, read only memory (ROM), Electrically Erasable Programmable ROM (EEPROM), Erasable Programmable ROM (EPROM), and resistance variable memory such as phase change random access memory (PCRAM), resistive random access memory (RRAM), and magnetoresistive random access memory (MRAM), among others.

Memory is also utilized as volatile and non-volatile data storage for a wide range of electronic applications, including, but not limited to personal computers, portable memory sticks, digital cameras, cellular telephones, portable music players such as MP3 players, movie players, and other electronic devices. Memory cells can be arranged into arrays, with the arrays being used in memory devices.

DETAILED DESCRIPTION

Figure 1A:
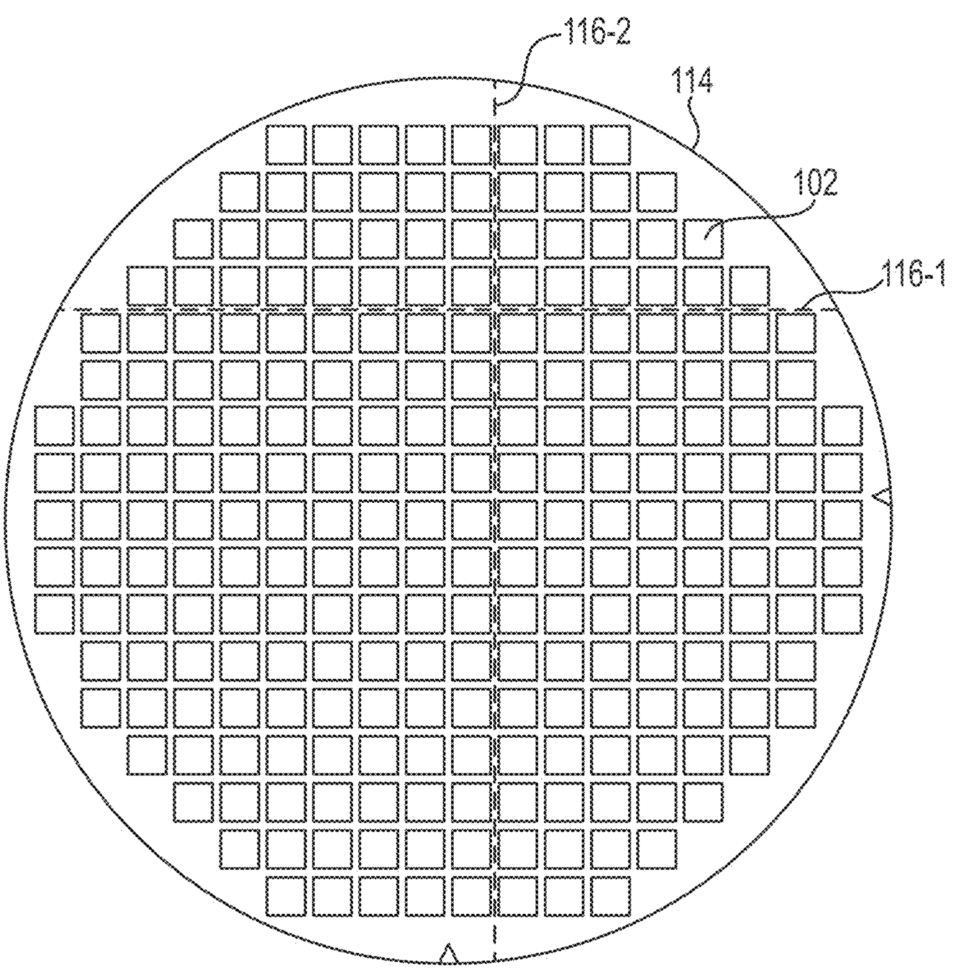
FIG. 1A is a top view of a memory wafer in accordance with a number of embodiments of the present disclosure.

The present disclosure includes apparatuses and methods related to a memory device for wafer-on-wafer formed memory logic. Inexpensive and energy-efficient logic devices have been proposed. Such devices can benefit from being tightly coupled to memory devices. Logic devices can be artificial intelligence (AI) accelerators such as deep learning accelerators (DLAs).

AI refers to the ability to improve a machine through "learning" such as by storing patterns and/or examples which can be utilized to take actions at a later time. Deep learning refers to a device's ability to learn from data provided as examples. Deep learning can be a subset of AI. Neural networks, among other types of networks, can be classified as deep learning. The low power, inexpensive design of deep learning accelerators can be implemented in internet-of-things (IoT) devices. The DLAs can process and make intelligent decisions at run-time. Memory devices including the edge DLAs can also be deployed in remote locations without cloud or offloading capability.

A three-dimensional integrated circuit (3D IC) is a metal-oxide semiconductor (MOS) IC manufactured by stacking semiconductor wafers or dies and interconnecting them vertically using, for example, through-silicon vias (TSVs) or metal connections, to function as a single device to achieve performance improvements at reduced power and smaller footprint than conventional two-dimensional processes. Examples of 3D ICs include hybrid memory cube (HMC) and high bandwidth memory (HBM), among others.

Methods for manufacturing 3D ICs include monolithic, die-on-die, die-on-wafer, chip-on-wafer, and wafer-on-wafer. Monolithic fabrication of 3D ICs generally involves providing a first layer of circuitry and/or electronic components, depositing a semiconductor material (e.g., silicon) on the first layer, and forming a second layer of circuitry/components on the first layer and/or electronic components by processing the deposited semiconductive material. The die-on-die, die-on-wafer, and chip-on-wafer processes include dicing one or both of the wafers prior to bonding. This may require aligning and bonding individual components formed on different wafers. In contrast, the wafer-on-wafer approach forms 3D ICs by building electronic components on two separate semiconductor wafers, which are subsequently aligned, bonded, and diced to form 3D ICs. Although processes for manufacturing 3D ICs are useful, they can present various challenges. For example, those processes may require expensive and time consuming alignment and bonding operations.

Aspects of the present disclosure address the above and other deficiencies. For instance, at least one embodiment of the present disclosure can provide high bandwidth via a wide bus between a memory die and a logic die bonded via a wafer-on-wafer bonding process. While the wide bus can provide for high bandwidth between the memory die and the logic die, the memory die can also operate according to a standardized input/output interface with a host, thus providing flexibility in the use of the memory. Various embodiments can be useful for artificial intelligence accelerators, machine learning, graph analysis, databases, fluid dynamics or other memory bandwidth intensive applications, image processing, language processing, virtual or augmented reality applications, genomics, proteomics, etc.

Embodiments of the present disclosure can provide a greater bandwidth from memory within a fixed power envelope compared to some previous approaches. For example, drones typically have limited power and space available. At least one embodiment of the present disclosure can provide improved inferences based on video obtained by a drone within that constrained power and space envelope. Another example implementation is providing power and thermal relief versus multiple standard memory packages on a common circuit board (e.g., graphics double data rate 6 (GDDR6) packages). Other advantages include improving top end performance with reduced power consumption in a fairly inexpensive package (e.g., more sensors could be added to an autonomous vehicle while still operating within a given power envelope).

An example implementation of one or more embodiments of the present disclosure is in a data center. Embodiments of the present disclosure can improve those efficiencies for a variety of applications. Wafer-on-wafer formed logic and memory dies can be combined in a network (e.g., a mesh network) and scaled up to perform various applications. Examples include a type-2 accelerator card, running training applications (e.g., on the fly business center data, operating on a database, etc.), among other examples. The efficiency of processes run in a data center is important for cost and energy efficiency. A compute express link (CXL) card could incorporate several wafer-on-wafer bonded logic and memory die.

An example implementation of one or more embodiments of the present disclosure is in 5G infrastructure. Smaller sized antennas with improved capabilities such as improved antenna alignment or steering, network intrusion detection, a low bandwidth link among 5G towers that can be provided to enable group intelligence and state (e.g., detect multiple intrusions across towers as evidence of a concentrated attack), improved mobility through network pass off of the state of inference of mobile devices between 5G towers, etc. 5G towers can be outfitted with cameras for additional municipal infrastructure awareness applications, for example. Rather than using the 5G bandwidth to transmit the camera data over a network, the camera data can be handled locally via a wafer-on-wafer bonded memory die and logic die to perform the municipal infrastructure awareness application without reducing performance of the 5G antenna. Such embodiments can also provide a lower power solution to handling the camera data versus a separate dedicated DLA to do the same. For example, a DLA can use 3 watts, a memory can use 2 watts, and a processor can use 1 watt to perform analysis of the camera data. However, according to the present disclosure the wafer-on-wafer bonded memory die and logic die (e.g., DLA in this example) can operate at 3 watts and replace the separate memory and accelerator devices, saving 2 watts in this example.

An example implementation of one or more embodiments of the present disclosure is in providing privacy for speech recognition applications. Typically, according to some previous approaches, speech recognition is performed by a local sensor sending data via a network (e.g., a public network) to a server where powerful processing can occur to provide the speech recognition functionality. However, according to at least one embodiment of the present disclosure, the greater bandwidth provided between the memory die and the logic die (e.g., a speech recognition die in this example) can allow the speech recognition (or at least a portion thereof) to be performed in greater locality to the sensor, potentially avoiding exposure over networks.

The figures herein follow a numbering convention in which the first digit or digits correspond to the drawing figure number and the remaining digits identify an element or component in the drawing. Similar elements or components between different figures may be identified by the use of similar digits. For example, 102 references element "02" in FIG. 1A, and a similar element is referenced as 302 in FIG. 3B. Analogous elements within a Figure may be referenced with a hyphen and extra numeral or letter. See, for example, elements 116-1, 116-2 in FIG. 1A. As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present invention and should not be taken in a limiting sense.

Figure 1B:
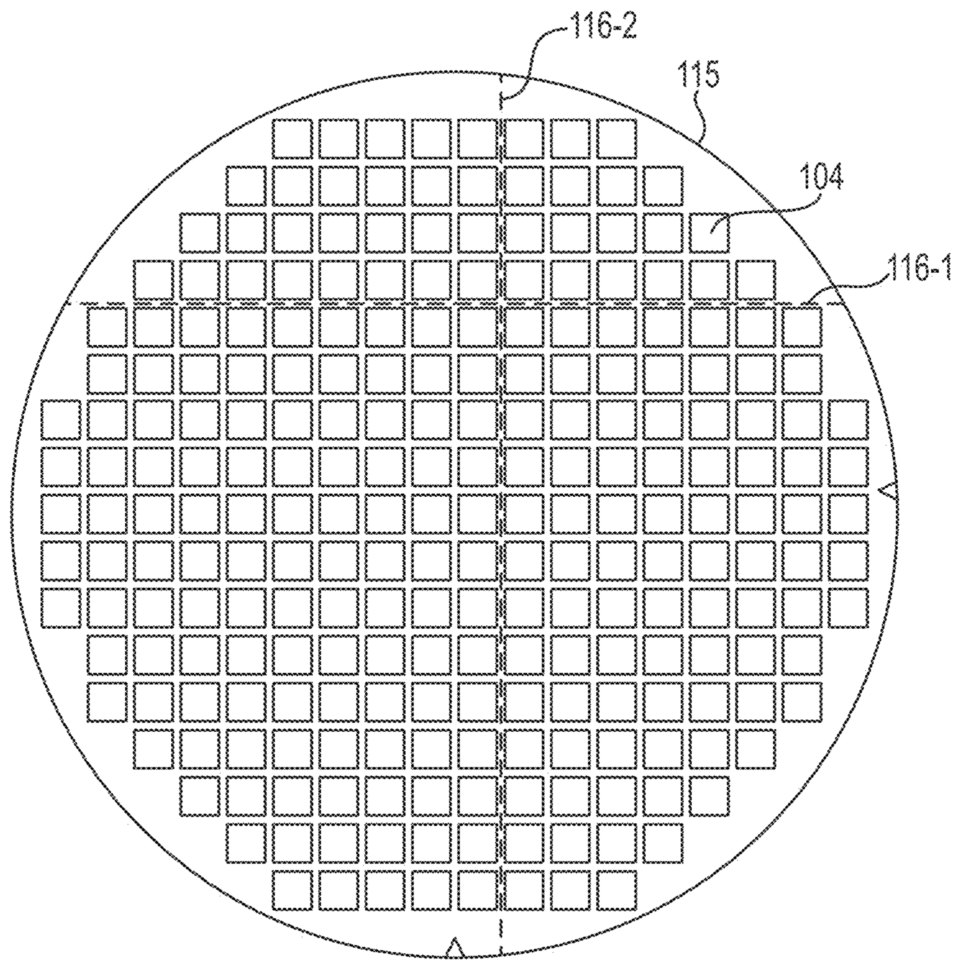
FIG. 1B is a top view of a logic wafer in accordance with a number of embodiments of the present disclosure.

FIG. 1A is a top view of a memory wafer in accordance with a number of embodiments of the present disclosure. FIG. 1B is a top view of a logic wafer in accordance with a number of embodiments of the present disclosure. As used in this disclosure, the term "wafer" can include, but is not limited to, silicon-on-insulator (SOI) or silicon-on-sapphire (SOS) technology, doped and undoped semiconductors, epitaxial layers of silicon supported by a base semiconductor foundation, and other semiconductor structures. Furthermore, when reference is made to a "wafer" or "substrate" in the following description, previous process steps may have been utilized to form regions or junctions in the base semiconductor structure or foundation.

As illustrated in FIGS. 1A-1B, the wafers 114, 115 can have a round peripheral edge. The wafers 114, 115 can include a number of dies (e.g., the memory die 102 illustrated in FIG. 1A or the logic device die 104 illustrated in FIG. 1B) having streets 116 (e.g., streets 116-1, 116-2) located therebetween. As used herein, streets 116 may be referred to as saw streets or scribe streets. The streets 116 can be paths along which a tool may cut in order to singulate the dies. As used herein, the term "singulate" refers to separating conjoined units into individual units. Prior to a cutting, the streets 116 may be etched to a particular depth to help guide a saw blade. Furthermore, one or more side marks along the edge of the top of the wafers 114, 115 can be used to align the saw blade before cutting. In many cases, and as shown in FIGS. 1A-1B, the dies can be formed on the wafers 114, 115 such that the streets 116 are formed in perpendicular rows and columns.

The dies can comprise electronic devices. In some embodiments, each die on a particular wafer can be a same type of device. For example, each die on the wafer 114 illustrated in FIG. 1A can be a memory die 102 and each die on the wafer 115 illustrated in FIG. 1B can be a logic device 104. As used herein, an electronic device can include transistors, capacitors, diodes, memory devices, processors, other devices, and/or integrated circuits. Examples of the logic device 104 include application specific integrated circuits (ASICs) such as a DLA, a radio frequency communication circuit, a gene sequencing circuit, a video or imaging circuit, an audio circuit, a sensor circuit, a radar circuit, packet routing circuit, intrusion-detection circuit, safety monitoring circuit, cryptographic circuit, blockchain circuit, smart sensor circuit, 5G communication circuit, etc.

Each of the plurality of memory die can include an array of memory cells configured on a die or chip and a plurality of local input/output (LIO) lines for communication of data on the die or chip. Further, each of the plurality of memory die can include a plurality of transceivers associated with (e.g., coupled to) the plurality of LIO lines, wherein the plurality of transceivers are configured to selectively enable communication of the data to one or more devices off the die or chip. Further, each of the plurality of memory die can include memory-to-logic circuitry coupled to the plurality of transceivers and configured to be coupled to a logic die via a wafer-on-wafer bond. In some embodiments, more than one of the plurality of memory die share memory-to-logic circuitry. In some embodiments, at least one memory-to-logic circuitry is configured to be coupled to a plurality of logic dies via the wafer-on-wafer bond.

Testing infrastructure can be formed in association with the wafers 114, 115 and/or the dies 102, 104. Embodiments of the present disclosure can be implemented without changing the fabrication and/or use of the testing infrastructure. If testing of an individual die 102, 104 indicated that the die was bad, according to some previous approaches, the die 102, 104 would not be used in an electronic device. However, according to at least one embodiment of the present disclosure, the die 102, 104 can be abandoned in place so that the remainder of the wafer 114, 115 can be used. The counterpart die 102, 104 corresponding to the bad memory die 102, 104 can be disabled.

In some previous approaches, after fabrication of the electronic devices on the wafers 114, 115, the wafers 114, 115 can be diced (e.g., by a rotating saw blade cutting along the streets 116). However, according to at least one embodiment of the present disclosure, after fabrication of the devices on the wafers 114, 115, and prior to dicing, the wafers 114, 115 can be bonded together by a wafer-on-wafer bonding process. Subsequent to the wafer-on-wafer bonding process, the dies can be singulated. The memory wafer 114 can be bonded to the logic wafer 115 in a face-to-face orientation meaning that their respective substrates (wafers) are both distal to the bond while the memory dies and logic dies are proximal to the bond.

In some embodiments, the size of the devices on the first wafer 114 are the same as the size of the devices on the second wafer 115 and the streets 116 on the first wafer 114 are in a same relative position as the streets 116 on the second wafer 115. This enables individual memory die 102 and logic die 104 to be singulated together as a single package after the wafers 114, 115 are bonded together.

Although not specifically illustrated, in some embodiments, the size of the devices on the first wafer 114 and the second wafer 115 are proportionally different. For example, a logic die 104 on the second wafer 115 can have the same footprint as four memory die 102 on the first wafer 114. When the wafers 114, 115 are bonded together, the four memory die 102 and one logic die 104 can be singulated as a single package. As another example, the memory die 102 on the first wafer 114 can have the same footprint as four logic dies 104 on the second wafer 115. When the wafers 114, 115 are bonded together, the four logic die 104 and one memory die 102 can be singulated as a single package, which may be referred to as a network-on-wafer package. Embodiments are not limited to a 4:1 ratio of die sizes.

Embodiments including differently sized memory dies 102 and logic dies 104 may further benefit from the testing described above. For example, for logic dies 104 that are smaller than memory dies 102, the dies 102, 104 can be tested and the wafers 114, 115 can be rotated before bonding such that a greatest possible number of known good logic dies 104 are bonded to known good memory dies 102. Analogously, for memory dies 102 that are smaller than logic dies 104, the dies 102, 104 can be tested and the wafers 114, 115 can be rotated before bonding such that a greatest possible number of known good memory dies 102 are bonded to known good logic dies 104. Different memory wafers 114 and logic wafers 115 can be mixed and matched to provide a greatest combination of known good memory dies 102 and logic dies 104, regardless of whether the dies 102, 104 are differently sized.

Whichever wafer 114, 115 includes the smaller devices will have some streets 116 that are not intended to be cut. Additional connections (e.g., metal layers) can be formed across these streets 116 since they will not be cut. The additional connections across streets 116 can be used to connect multiple individual memory die 102 or logic die 104 to each other prior to the wafer-on-wafer bonding process. Such embodiments can thus create wafer level networks of memory die 102 or logic die 104. In at least one embodiment, the first wafer 114 can include multiple networked memory die 102 forming a wafer-scale memory device. The networks can be peer-to-peer networks, for example.

Figure 1C:
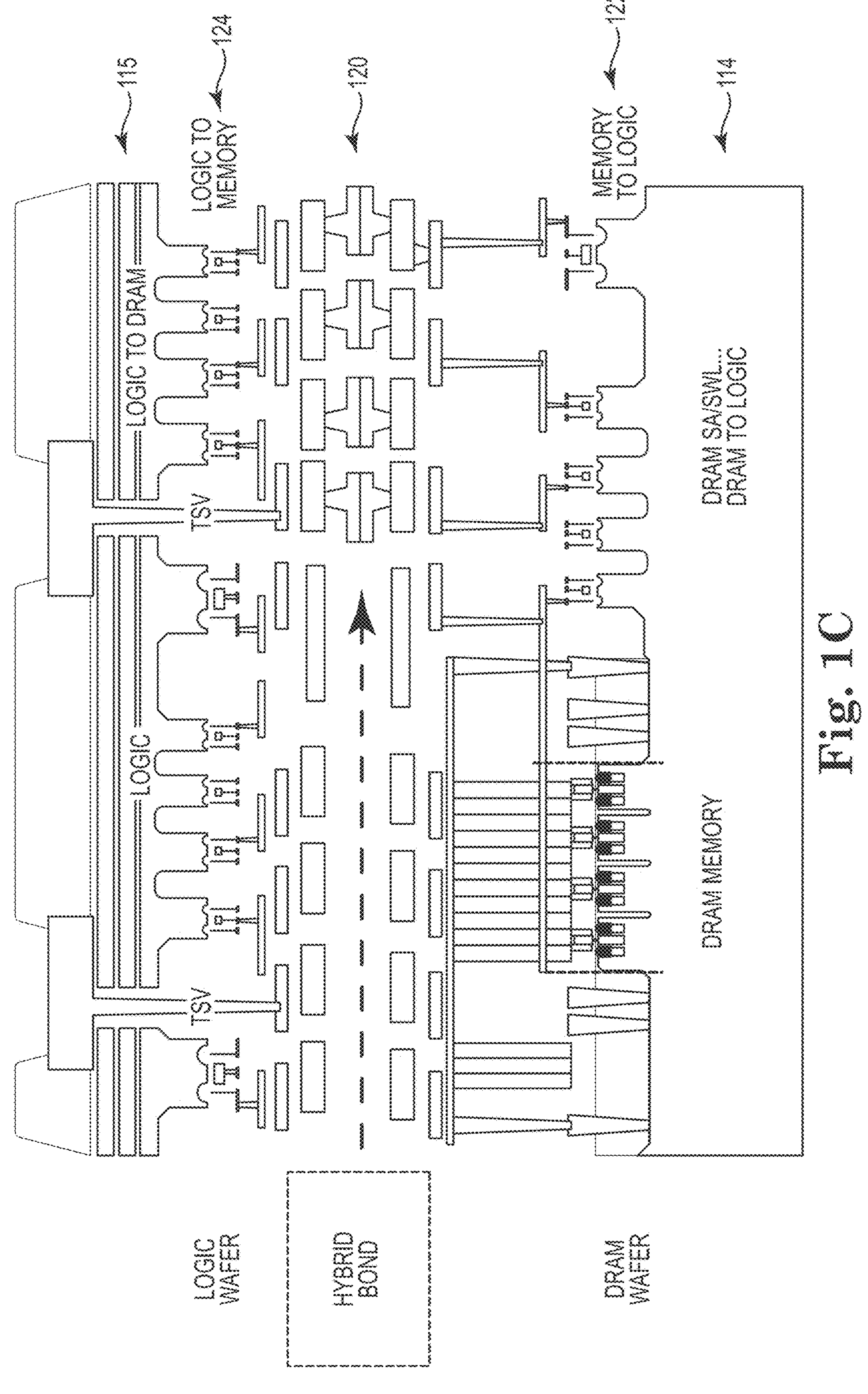
FIG. 1C is a cross-section of a portion of the memory wafer bonded to the logic wafer in accordance with a number of embodiments of the present disclosure.

FIG. 1C is a cross-section of a portion of the memory wafer 114 bonded to the logic wafer 115 in accordance with a number of embodiments of the present disclosure. The memory wafer 114 includes memory-to-logic circuitry 122 formed thereon. The memory-to-logic circuitry 122 is configured to provide an electrical connection and signaling for the transfer of data and/or control signals between at least one memory die of the memory wafer 114 and at least one logic die of the logic wafer 115. In at least one embodiment, the memory-to-logic circuitry can include as few as two additional metal layers beyond what is typically included for a DRAM memory die. The logic wafer 115 includes logic-to-memory circuitry 124 formed thereon. The logic-to-memory circuitry 124 is configured to provide an electrical connection and signaling for the transfer of data and/or control signals between at least one logic die of the logic wafer 115 and at least one memory die of the memory wafer 114. A bond 120 is formed between the memory-to-logic circuitry 122 of the memory wafer 114 and the logic-to-memory circuitry 124 of the logic wafer 115 in the wafer-on-wafer bonding process. The bond 120 may be referred to as a hybrid bond or a wafer-on-wafer bond herein. The bond 120 can include one or more of a metal bond and direct dielectric-dielectric bond. The bond 120 enables the transmission of electrical signals between the logic-to-memory circuitry 124 and the memory-to-logic circuitry 122.

The memory-to-logic circuitry 122 of the memory wafer 114 and/or the bond 120 can include bond pads at the transceiver, which can be associated with an LIO prefetch bus and/or sense amplifier (sense amp) stripe. In one example, one sense amp stripe includes 188 LIO connection pairs covering 9 array cores and 9216 pairs per channel. In another example, one sense amp stripe includes 288 LIO connection pairs and 4608 pairs per channel. Embodiments are not limited to these specific examples. The transceivers are described in more detail herein. The interconnect load of the bond 120 can be less than 1.0 femtofarads and 0.5 ohms. In one example implementation, the maximum number of rows of memory capable of being activated at one time (e.g., 32 rows) can be activated and transmit data via the bond 120 to the corresponding logic dies of the logic wafer 115. The memory-to-logic circuitry 122 and/or the bond 120 can include at least one power and at least one ground connection per transceiver (e.g., sense amp stripe). In at least one embodiment, the power connection is such that it allows activation of multiple rows of memory at once. In one example, the wafer-on-wafer bonding provides 256 k data connections at a 1.2 micrometer pitch.

In some embodiments, the bond 120 can include analog circuitry (e.g., jumpers) without transistors in the path between the memory die 102 and the logic die 104. One die 102, 104 can drive a signal therebetween and the other die 102, 104 can sink the signal therebetween (e.g., rather than passing signals between the dies 102, 104 via logic gates). In at least one embodiment, the bond 120 can be formed by a low temperature (e.g., room temperature) bonding process. In some embodiments, the bond 120 can be further processed with an annealing step (e.g., at 300 degrees Celsius).

Although not specifically illustrated, in at least one embodiment a redistribution layer can be formed between the memory wafer 114 and the logic wafer 115. The redistribution layer can enable compatibility of a single memory design to multiple ASIC designs. The redistribution layer can enable memory technologies to scale without necessarily scaling down the logic design at the same rate as the memory technology (e.g., circuitry on the memory die 102 can be formed at a different resolution than the circuitry on the logic die 104 without having to adjust the bond 120 and/or other circuitry between the memory die 102 and the logic die 104).

Figure 1D:
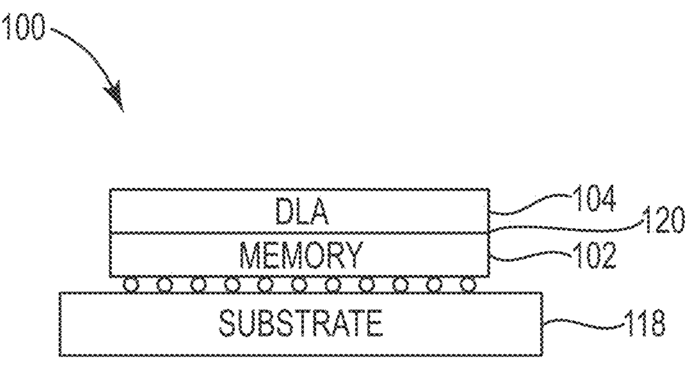
FIG. 1D illustrates a portion of the bonded wafers including a memory die and a logic die after dicing in accordance with a number of embodiments of the present disclosure.

FIG. 1D illustrates a portion of the bonded wafers including a memory die 102 and a logic die 104 after dicing in accordance with a number of embodiments of the present disclosure. The memory die 102 is illustrated as being bonded to a substrate 118, however, in at least one embodiment, the logic die 104 can be bonded to the substrate 118 instead of the memory die 102. The substrate 118, memory die 102, bond 120, and logic die 104 can form a system 100, such as an integrated circuit, configured to perform one or more desired functions. Although not specifically illustrated, the substrate 118 can include additional circuitry to operate, control, and/or communicate with the memory die 102, logic die 104, and or other off-chip devices.

According to at least one embodiment of the present disclosure, the typical functionality of the memory die 102 does not change for typical memory operations. However, data can alternatively be transferred from the memory die 102 to the logic die 104 directly via the bond 120 instead of being routed through the typical input/output circuitry of the memory die 102. For example, a test mode and/or refresh cycle of the memory die 102 can be used to transfer data to and from the logic die 104 via the bond 120 (e.g., via LIOs of the memory die 102). Using the refresh cycle for an example existing DRAM memory device, with 8 rows per bank active and a refresh cycle time of 80 nanoseconds (versus 60 nanoseconds for a single row) with 4 banks in parallel and 16 nanosecond bank sequencing, the bandwidth would be 443 gigabytes/second. However, according to at least one embodiment of the present disclosure, with the wafer-on-wafer bond 120, with 32 rows per bank active, the refresh cycle time can approach 60 nanoseconds for 32 banks in parallel and without bank sequencing, the bandwidth is 5 terabytes/second using 8 watts. Such a significant bandwidth of data being sent from the memory device would overwhelm a typical interface and/or host device. However, certain logic devices (such as a DLA) can be configured to make use of that data bandwidth via the connections provided by the bond 120. Reduced off-chip movement of data can help reduce the power consumption associated with operating the memory in this fashion.

Although not specifically illustrated, multiple memory die 102 can be stacked on one another via a bond analogous to the bond 120. Such additional memory die 102 can include memory-to-memory circuitry analogous to the memory-to-logic circuitry 122 illustrated in FIG. 1C. Alternatively, or additionally, TSVs can be used for communication of data between or through stacked memory die 102. The bond pads between stacked memory die 102 can be at locations that are replicated on stacked memory die 102 in a vertical orientation (as illustrated) such that the stacked memory die 102 are in alignment. The stacked memory die 102 can be formed by a conventional process or by wafer-on-wafer bonding (between different memory wafers) in different embodiments.

Although not specifically illustrated, the die that is bonded to the substrate 118 (e.g., the memory die 102 (as illustrated) or the logic die 104) can have TSVs formed therein to enable communication with circuitry external to the memory die 102 and logic die 104. The TSVs can also be used to provide power and ground contacts. Compared to the contacts provided by wafer-on-wafer bonding, TSVs generally have greater capacitance and a larger pitch and do not have as great of a bandwidth.

Although not specifically illustrated, in some embodiments an additional component can be bonded to the system 100. For example, a thermal solution component can be bonded to the top of the logic die 104 to provide cooling for the system 100. The physically close connection between the logic die 104 and the memory die 102 may generate heat. The thermal solution can help dissipate heat for the system 100.

Although not specifically illustrated, in some embodiments an additional component (non-volatile memory) can be bonded to the system 100 (e.g., in order to persistently store a model for the artificial neural network (ANN)). However, in some embodiments, the non-volatile memory is not necessary because the models may be relatively small and frequently updated.

Figure 2A:
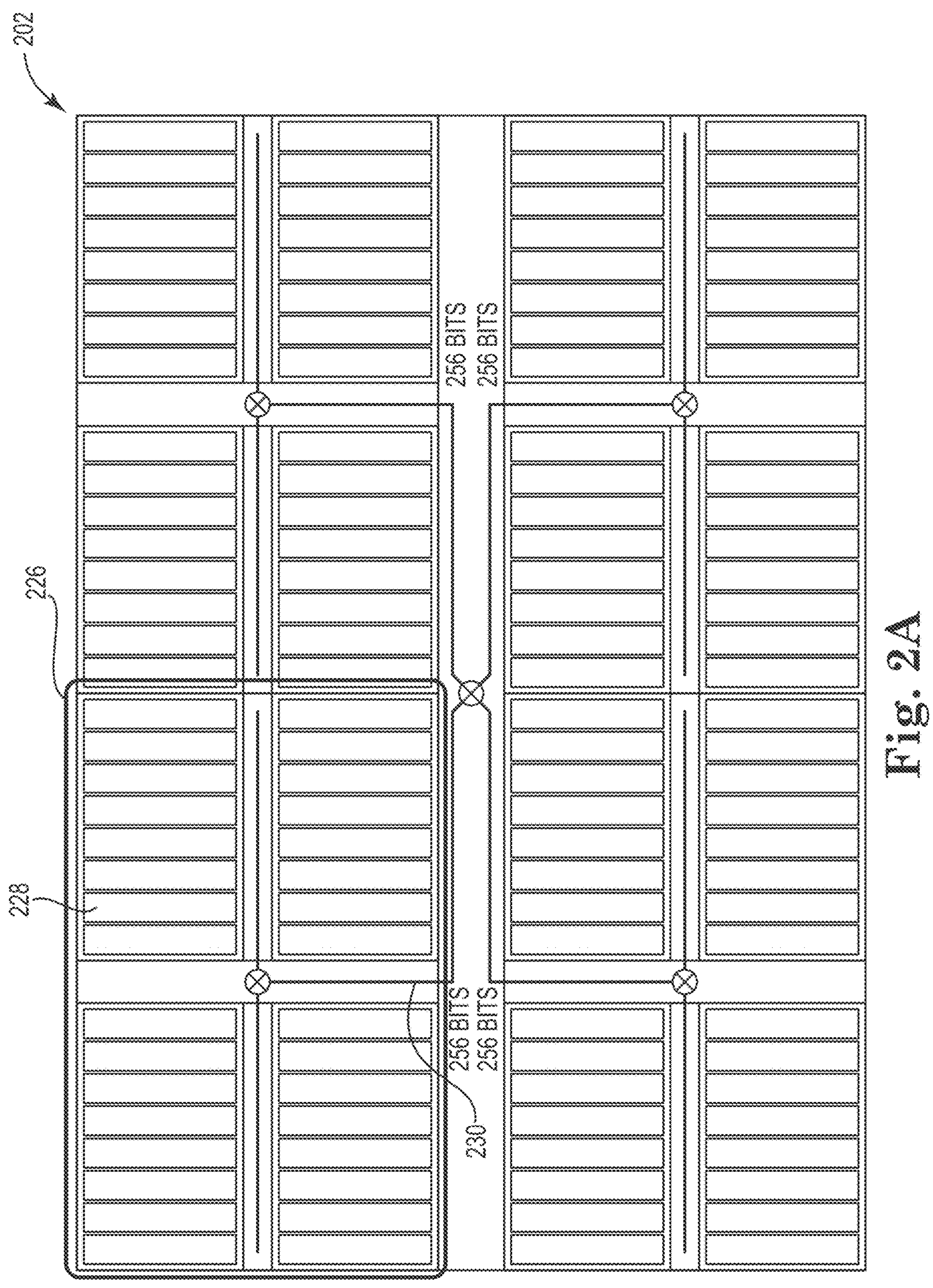
FIG. 2A illustrates a circuit diagram of a memory die in accordance with a number of embodiments of the present disclosure.

FIG. 2A illustrates a circuit diagram of a memory die 202 in accordance with a number of embodiments of the present disclosure. The example memory die 202 includes 16 memory banks 228 arranged in bank groups 226 of 4 banks. Each bank group 226 is coupled to a global data bus 230 (e.g., a 256-bit wide bus). Embodiments are not limited to these specific examples. The global data bus 230 can be modeled as a charging/discharging capacitor. The global data bus 230 can conform to a memory standard for sending data from the memory die 202 via an IO bus. However, although not specifically illustrated in FIG. 2A, according to at least one embodiment of the present disclosure, the memory die 202 can include additional transceivers for communicating data with a logic die via a wafer-on-wafer bond.

Figure 2B:
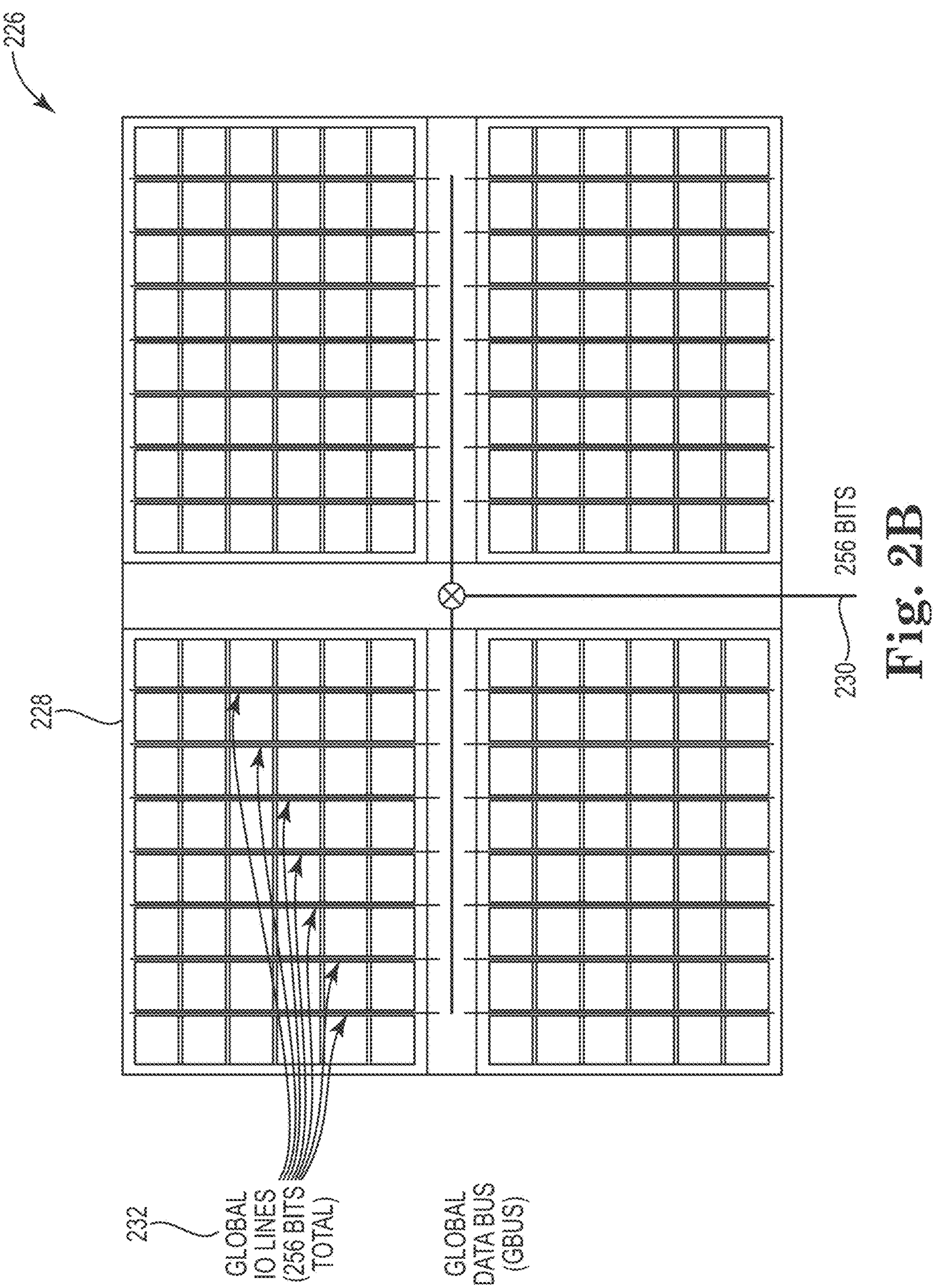
FIG. 2B illustrates a circuit diagram of a memory bank group in accordance with a number of embodiments of the present disclosure.

FIG. 2B illustrates a circuit diagram of a memory bank group 226 in accordance with a number of embodiments of the present disclosure. The memory bank group 226 can include 4 memory banks 228 as illustrated, or another quantity of banks. Each memory bank 228 can include respective global input/output (I/O) lines 232 that ultimately connect to the global I/O bus 230. In this example, the bank group 226 is capable of transmitting 256 bits at one time.

Figure 2C:
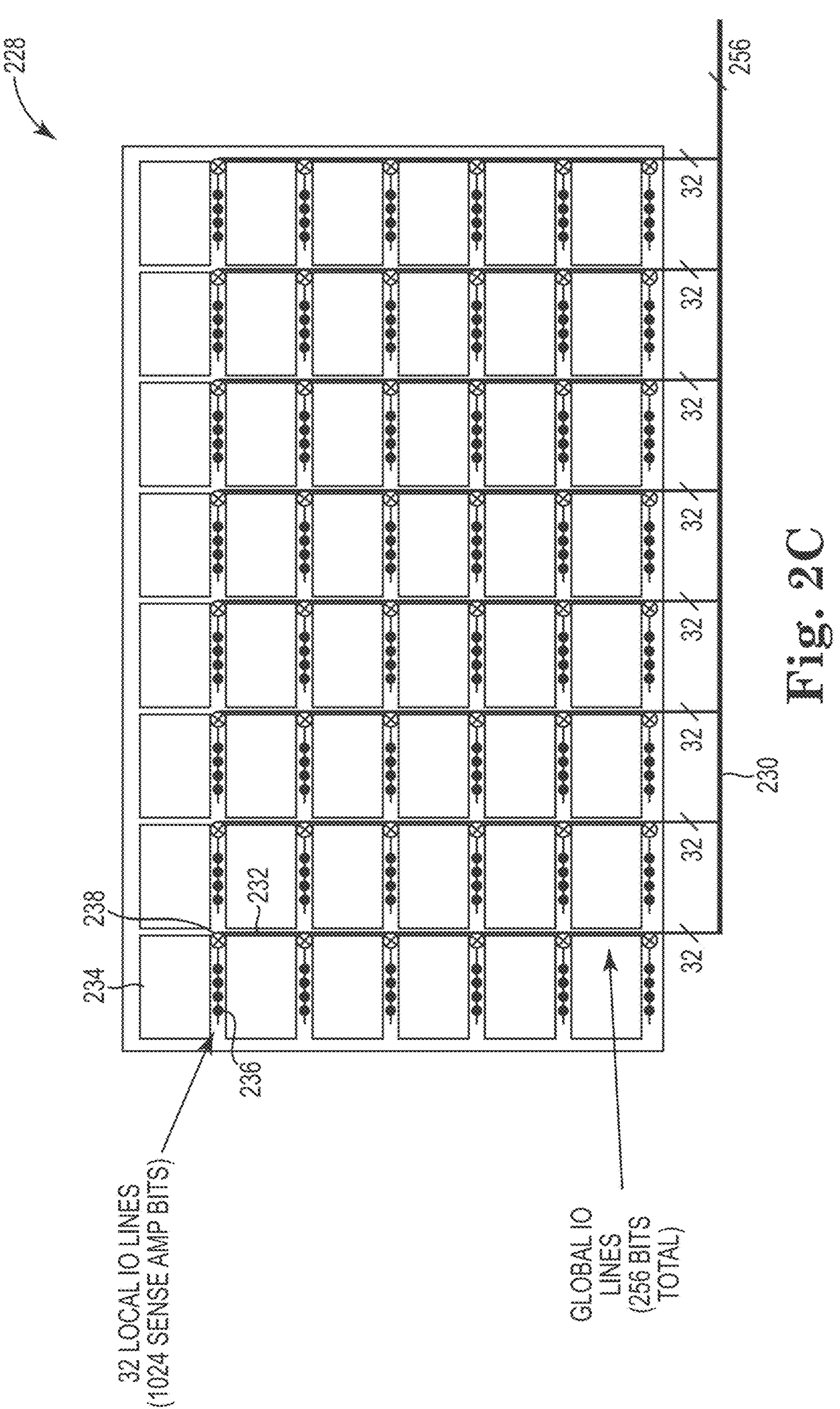
FIG. 2C illustrates a memory bank in accordance with a number of embodiments of the present disclosure.

FIG. 2C illustrates a memory bank 228 in accordance with a number of embodiments of the present disclosure. The memory bank 228 includes a quantity of memory tiles 234, each including a respective quantity of LIO lines 236 on the die or chip represented by the filled dots. Although only four filled dots are illustrated, the four filled dots can represent any number of LIO lines (e.g., 32 LIO lines). Each tile 234 can include a respective array of memory cells configured on the die or chip coupled to sense lines and access lines of the die or chip, wherein the array of memory cells includes a quantity of rows and a quantity of columns of memory cells (e.g., 1024×1024). For example, each tile can include 32 LIOs 236. In some embodiments, each LIO line can be coupled to a respective global I/O line (e.g., 32 LIOs 236 can be coupled to 32 global I/O lines 232). Each plurality of subsets of the sense lines is coupled to a respective IO line, and the LIOs 236 in each tile are coupled to a respective global I/O line 232. In some embodiments, each LIO 236 is coupled to a respective transceiver. In some embodiments, each global I/O line 232 is coupled to respective transceivers (e.g., transceiver 238 as illustrated in FIG. 2C). For ease of illustration, the transceiver 238 is shown as a single component connected between the LIO lines 236 and a global I/O line 232, however, each LIO line 236 can have an independent transceiver 238 or circuitry connected to a transceiver 238 that multiplexes a quantity of LIO lines 236.

A plurality of tiles can be coupled to the global I/O line (e.g., I/O bus). LIOs 236 can be coupled to a global I/O line 232 for communication of data on the die or chip via the global I/O bus 230. Each transceiver 238 can be selectively enabled to transmit data off-chip (e.g., to a logic die via a wafer-on-wafer bond) instead of to the corresponding global I/O line 232. As used herein, communication of data on the die or chip means that signals indicative of data are transmitted within a memory die or memory chip. As used herein, communication of data to one or more devices off the die or chip means that signals indicative of data are transmitted between a memory die or memory chip and a logic die or logic chip. Multiple sense amplifiers can be multiplexed into a single transceiver 238. Each transceiver 238 can be coupled to a respective contact with a corresponding logic die via a wafer-on-wafer bond. The wafer-on-wafer bond provides pitch control sufficiently fine to allow for such contacts, which would otherwise not be possible.

In at least one embodiment, the transceiver 238 can receive an enable/disable command from the corresponding logic die coupled thereto (e.g., as opposed to receiving the command from a host). In some embodiments, the enable/disable command can be received by multiple transceivers 238 (e.g., the enable/disable command can cause signals indicative of data from a particular row in each bank 228 to be transferred via the corresponding transceivers 238). The control and operation of the multiple transceivers 238 is similar to having thousands of memory controllers, except that they transfer data rather than controlling all operations. Such operation can be beneficial, for example, for applications that involve massively parallel memory access operations. For an example memory device that is configured to include an 8-kilobit row, 256 bits of data can be prefetched per transceiver 238. Therefore, each transceiver 238 can have 256 bits bonded out. In other words, at least one embodiment of the present disclosure can transfer 256 bits of data for each 8 kilobits of stored data (in this example architecture). In contrast, according to some previous approaches with an analogous architecture, a typical memory interface (e.g., via a global I/O) would only be able to transfer 256 bits for 4 gigabits of stored data.

Figure 2D:
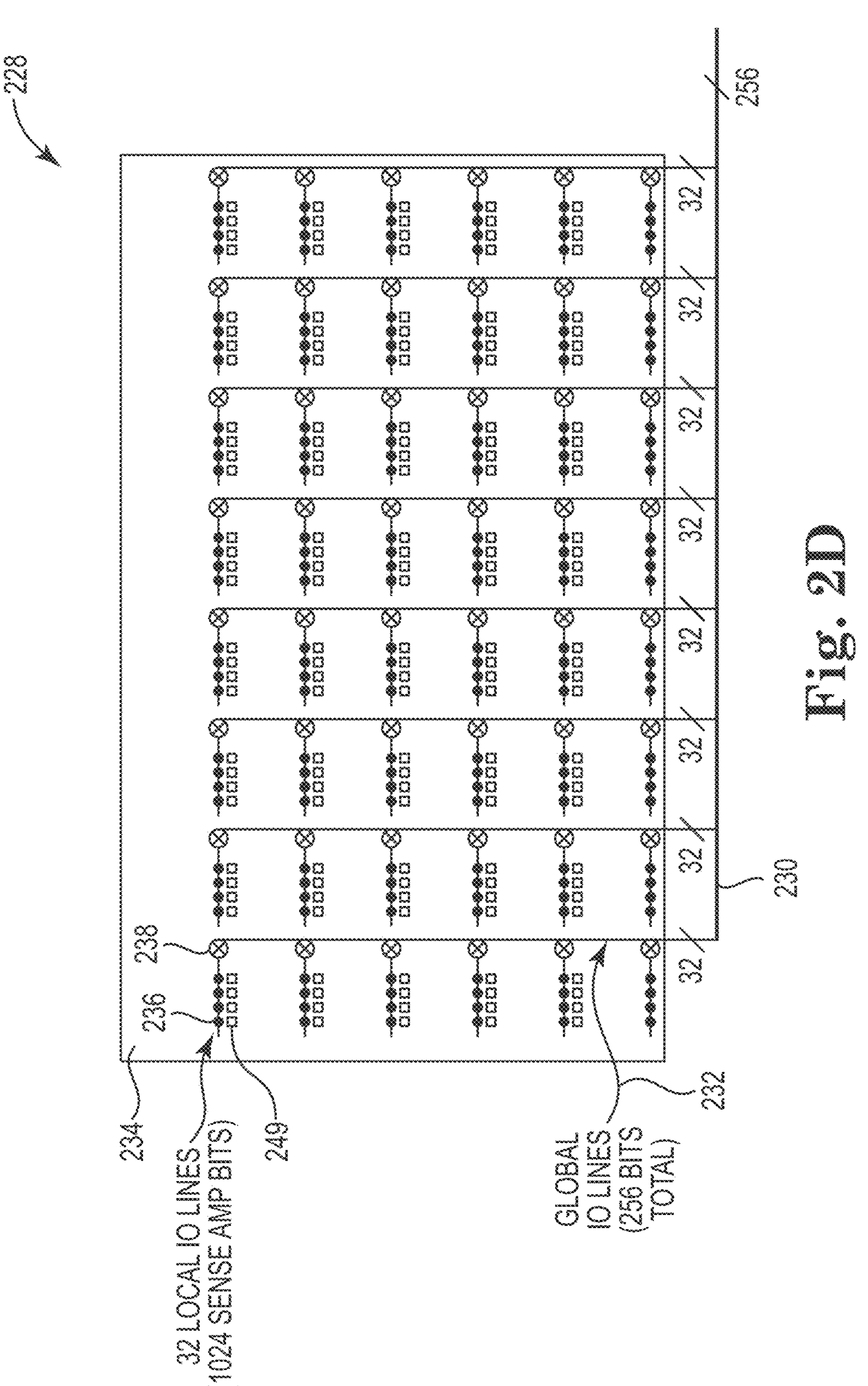
FIG. 2D illustrates a memory bank in accordance with a number of embodiments of the present disclosure.

FIG. 2D illustrates a memory bank 228 in accordance with a number of embodiments of the present disclosure. As stated in FIG. 2C, the memory bank 228 includes a quantity of memory tiles 234, each including a respective quantity of LIO lines 236 represented by the filled dots. Further, circuitry 249 can be coupled to each of the LIO lines 236. Circuitry 249 can include a sense amplifier, a multiplexor, and a transceiver. In some embodiments, the circuitry 249 can include multiple sense amplifiers, multiple multiplexors, and multiple transceivers. For example, the circuitry 249 can include a number of sense amplifiers such that there are 32 sense amplifiers per LIO 236 coupled to the circuitry 249.

Figure 2E:
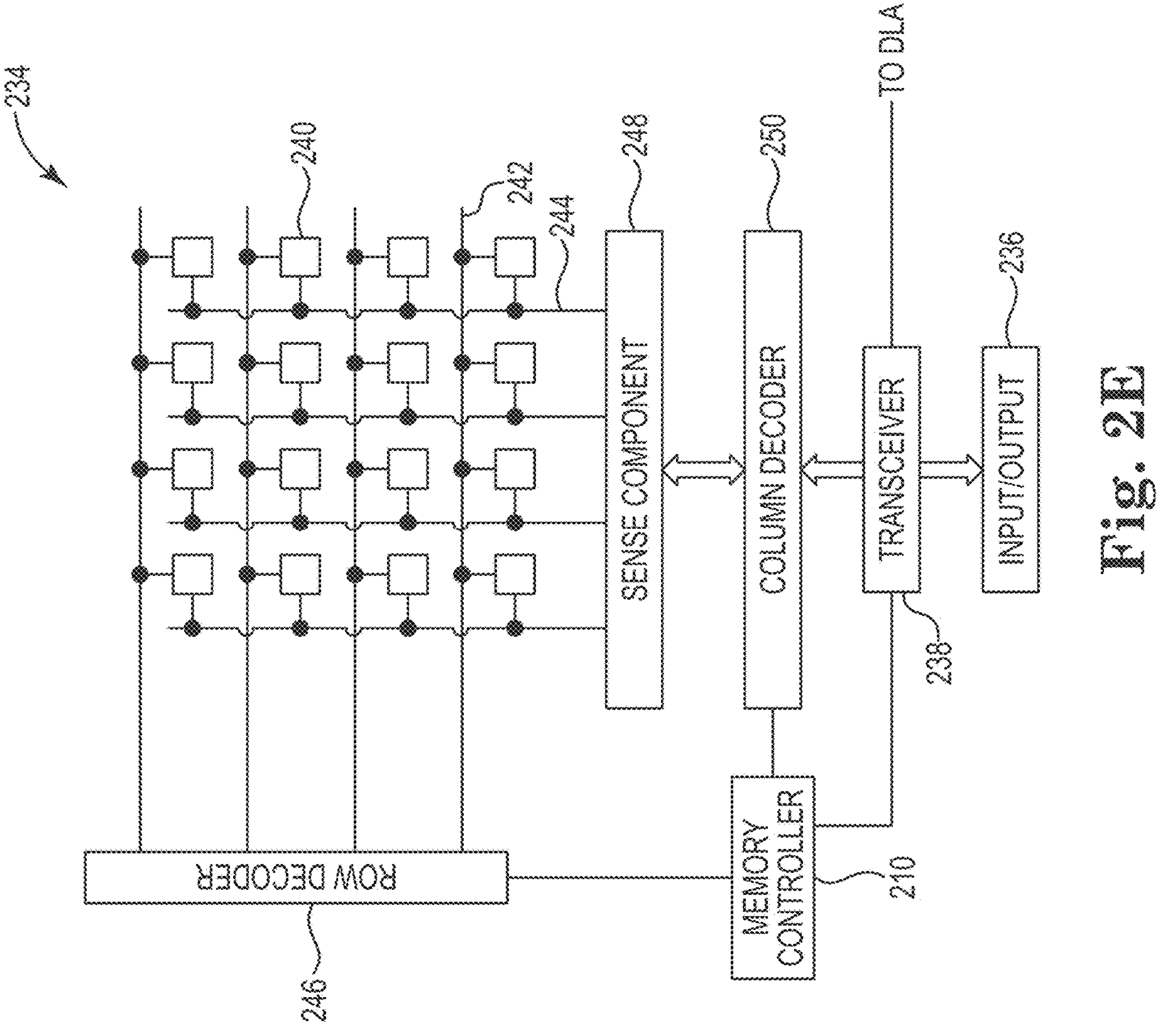
FIG. 2E illustrates a memory tile in accordance with a number of embodiments of the present disclosure.

FIG. 2E illustrates a memory tile 234 in accordance with a number of embodiments of the present disclosure. The memory tile 234 includes memory cells 240 that are programmable to store different states. Each memory cell 240 may be programmable to store two states, denoted as a logic 0 and a logic 1. In some cases, a memory cell 240 is configured to store more than two logic states. A memory cell 240 may include a capacitor to store a charge representative of the programmable states; for example, a charged and uncharged capacitor may represent two logic states. DRAM architectures may commonly use such a design, and the capacitor employed may include a dielectric material with linear electric polarization properties.

Operations such as reading and writing may be performed on memory cells 240 by activating or selecting the appropriate access line 242 and sense lines 244. Activating or selecting an access line 242 or a sense line 244 may include applying a voltage potential to the respective line. Access lines 242 and sense lines 244 may be made of conductive materials. In some examples, access lines 242 and sense lines 244 are made of metals (e.g., copper, aluminum, gold, tungsten, etc.). Each row of memory cells 240 are connected to a single access line 242, and each column of memory cells 240 are connected to a single sense line 244. The intersection of an access line 242 and a sense line 244 may be referred to as an address of a memory cell 240.

In some architectures, the storage component of a memory cell 240, e.g., a capacitor, may be electrically isolated from the sense line 244 by a selection device. The access line 242 may be connected to and may control the selection device. For example, the selection device may be a transistor and the access line 242 may be connected to the gate of the transistor. Activating the access line 242 results in an electrical connection between the capacitor of a memory cell 240 and its corresponding sense line 244. The sense line 244 may then be accessed to either read or write the memory cell 240.

Accessing memory cells 240 may be controlled through a row decoder 246 and a column decoder 250. For example, a row decoder 246 may receive a row address from the memory controller 210 and activate the appropriate access line 242 based on the received row address. Similarly, a column decoder 250 receives a column address from the memory controller 210 and activates the appropriate sense lines 244. Thus, by activating an access line 242 and sense lines 244, memory cells 240 may be accessed. The column decoder 250 can be coupled to each subset of the sense lines 244 and the respective LIO line.

Upon accessing, a memory cell 240 may be read, or sensed, by sense component 248. For example, sense component 248 may compare a signal (e.g., a voltage) of the relevant sense line 244 to a reference signal (not shown) in order to determine the stored state of the memory cell 240. If sense line 244 has a higher voltage than the reference voltage, then sense component 248 may determine that the stored state in memory cell 240 was a logic 1 and vice versa. The sense component 248 can be coupled to sense lines 244 and each subset of the sense lines 244 is coupled to a respective LIO line 236 for communication of data on the die or chip.

The sense component 248 may include various transistors or amplifiers in order to detect and amplify a difference in the signals, which may be referred to as latching. In some cases, sense component 248 may include or be referred to as a sense amplifier. The sense component 248 can represent a stripe of multiple sense amplifiers. The detected logic state of memory cell 240 may then be output through column decoder 250 and to an LIO 236. In some embodiments, a transceiver can be coupled to each respective sense amplifier 248 and configured to retrieve data from the sense amplifier 248.

However, according to at least one embodiment of the present disclosure, the memory controller 210 can send a signal to the transceiver 238, to selectively route the signals indicative of data off-chip (e.g., to a logic die "to DLA") instead of to the normal IO path (e.g., via the LIO 236). The memory controller 210 can cause the transceiver 238 to either allow signals indicative of data to either continue on the typical path (e.g., via the LIO 236) or be sent to a wafer-on-wafer bonded logic die via the bonds and contacts described herein. The illustrated path from the transceiver 238 ("To DLA") is a representation of the electrical pathway between the memory tile 234 and the corresponding logic die (not illustrated in FIG. 2E). Embodiments of the present disclosure can preserve the functionality and fabrication of a standardized memory interface while allowing for the functionality and fabrication of an additional high bandwidth interface from the memory die to a logic die via the wafer-on-wafer bond. The transceiver 238 can extract signals indicative of data from near the sense component 248 and transfer it to the logic die.

In some embodiments, the transceiver 238 can be coupled between the column decoder 250 and the respective LIO line 236. Further, in some embodiments, the transceiver 238 can be embedded in the column decoder 250. Control circuitry (e.g., memory controller 210) coupled to the respective transceiver 238 can be configured to send a control signal to the transceiver 238 to selectively enable communication of the data to one or more devices off the die or chip.

Memory cells 240 may be set, or written, by activating the relevant access line 242 and sense lines 244. Activating an access line 242 electrically connects the corresponding row of memory cells 240 to their respective sense lines 244. By controlling the relevant sense lines 244 while the access line 242 is activated, memory cells 240 may be written (a logic value may be stored in the memory cell 240). The column decoder 250 may accept data, for example via the LIO 236, to be written to the memory cells 240.

However, according to at least one embodiment of the present disclosure, the transceiver can be configured to enable communication of data to one or more devices off the die or chip. For example, control circuitry (e.g., the memory controller 210) can be configured to send a control signal to the transceiver 238, to enable communication of the data to one or more devices off the die or chip by selectively routing signals indicative of data to or from off-chip (e.g., from a logic die) instead of to or from the normal IO path (e.g., via the LIO 236). The memory controller 210 can cause the transceiver 238 to either allow signals indicative of data to be received from the typical path (e.g., via the LIO 236) or be received from a wafer-on-wafer bonded logic die via the bonds and contacts described herein. In some embodiments, communication of data on the die or chip can occur on a first portion of a memory device and communication of data to one or more devices off the die or chip can occur in a second portion of a memory device simultaneously. Operation of the first portion of the memory device can be independent of operation of the second portion of the memory device. In some embodiments, the memory device can be a DRAM memory device.

A memory device can include a multiplexor coupled to the sense lines 244. The memory device can also include a transceiver 238 configured to receive a control signal to switch the memory device between a first mode of operation and a second mode of operation. In the first mode of operation, the transceiver 238 can be configured to enable communication of data on the die or chip. In some embodiments, communication of data to one or more devices off the die or chip can be disabled in the first mode of operation. In the second mode of operation, the transceiver 238 can be configured to enable communication of data to one or more devices off the die or chip. In some embodiments, communication of data on the die or chip can be disabled in the second mode of operation.

In some embodiments, signals indicative of data corresponding to the communication of data to one or more devices off the die or chip travel through the LIO lines. The LIO lines can couple memory dies to circuitry outside of the memory dies (e.g., to DLAs). Signals indicative of data can be transferred between the memory dies and circuitry outside of the memory dies through the LIO lines. In some embodiments, a bandwidth of the communication of data to one or more devices off the die or chip can be greater than a bandwidth of the communication of data on the die or chip. The bandwidth of the communication of data to one or more devices off the die or chip can be greater than the communication of data on the die or chip because the communication of data to one or more devices off the die or chip can involve more LIO lines than communication of data on the die or chip. For example, multiple LIO lines can be used to transfer data off-chip. However, one LIO line may be used to transfer data on-chip. Further, a sense amplifier of a memory die can be directly coupled to circuitry outside of the memory die. In such embodiments, data can be transferred off-chip at the speed the data leaves the sense amplifier. However, data being transferred on-chip can travel at the speed of the bandwidth of the global I/O.

In some memory architectures, accessing the memory cell 240 may degrade or destroy the stored logic state and re-write or refresh operations may be performed to return the original logic state to memory cell 240. In DRAM, for example, the capacitor may be partially or completely discharged during a sense operation, corrupting the stored logic state. Additionally, activating a single access line 242 may result in the discharge of all memory cells in the row; thus, several or all memory cells 240 in the row may need to be re-written. Some memory architectures, including DRAM, may lose their stored state over time unless they are periodically refreshed by an external power source. For example, a charged capacitor may become discharged over time through leakage currents, resulting in the loss of the stored information. Logic states may be re-written during a re-write operation or refreshed during a refresh operation.

The memory controller 210 may control the operation (e.g., read, write, re-write, refresh, etc.) of memory cells 240 through the various components, for example, row decoder 246, column decoder 250, and sense component 248. Memory controller 210 may generate row and column address signals in order to activate the desired access line 242 and sense lines 244. Memory controller 210 may also generate and control various voltage potentials used during the operation of memory tile 234. For example, memory controller 210 may operate a selection component to isolate a sense line 244 (e.g., from a corresponding capacitor)

during sensing. In general, the amplitude, shape, or duration of an applied voltage discussed herein may be adjusted or varied and may be different for the various operations for operating memory array. Furthermore, one, multiple, or all memory cells 240 within the memory tile 234 may be accessed simultaneously; for example, multiple or all cells of memory tile 234 may be accessed simultaneously during a reset operation in which all memory cells 240, or a group of memory cells 240, are set to a single logic state.

In some embodiments, an apparatus (e.g., memory device) can be configured to simultaneously access a first access line in a row of a first tile and a second access line in the same row of second tile for communication of the data. In this context, the "same row" means that the rows positionally correspond to each other (e.g., the rows line up if the tiles are positioned side-by-side). It does not necessarily mean that the rows are physically connected to each other. Further, a memory device can be configured to simultaneously access a first access line in a first row of a first tile and second access line in a second row of a second tile for communication of data. In this context, the first and second rows do not positionally correspond to each other (e.g., they do not line up if positioned side-by-side). The memory device can also be configured to access each tile synchronously or asynchronously. As used herein, asynchronously access each tile refers to accessing different tiles at different times. Asynchronously accessing the tiles can avoid large power spikes that can result from accessing a certain amount of tiles simultaneously.

Figure 3A:
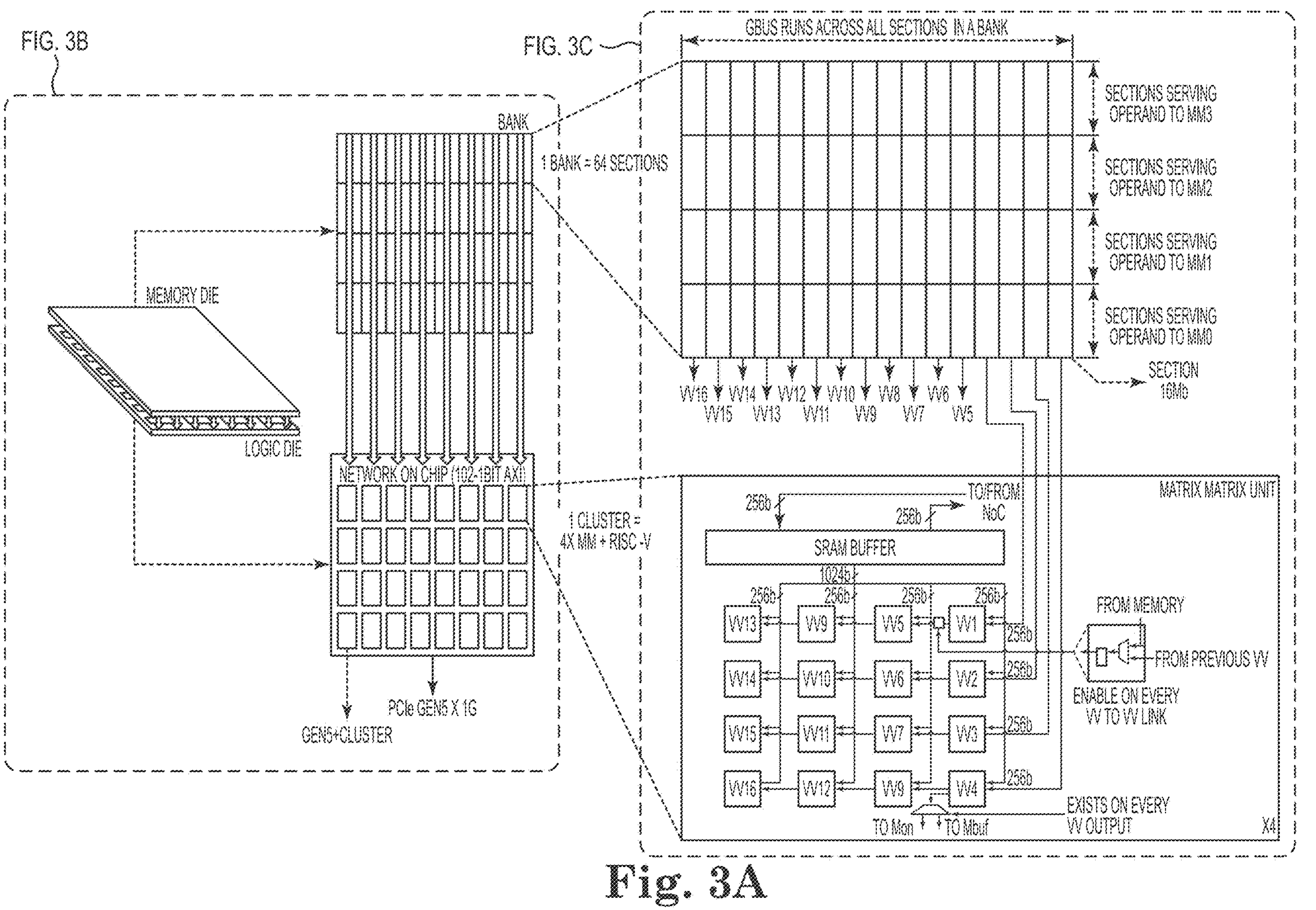
FIG. 3A is a block diagram of an example of a memory-logic architecture in accordance with a number of embodiments of the present disclosure.
Figure 3B:
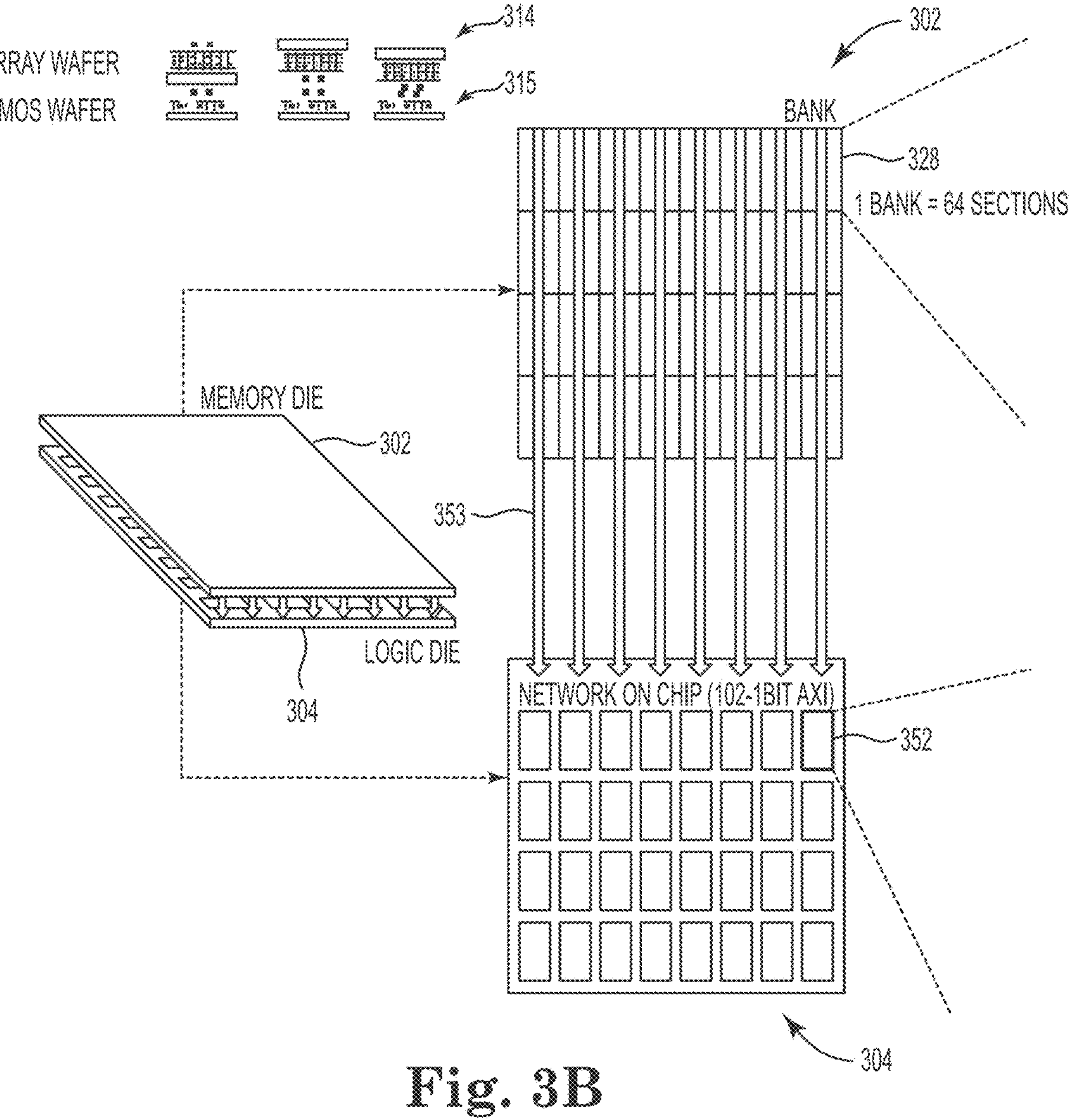
FIG. 3B is a block diagram of a first portion of the architecture illustrated in FIG. 3A.
Figure 3C:
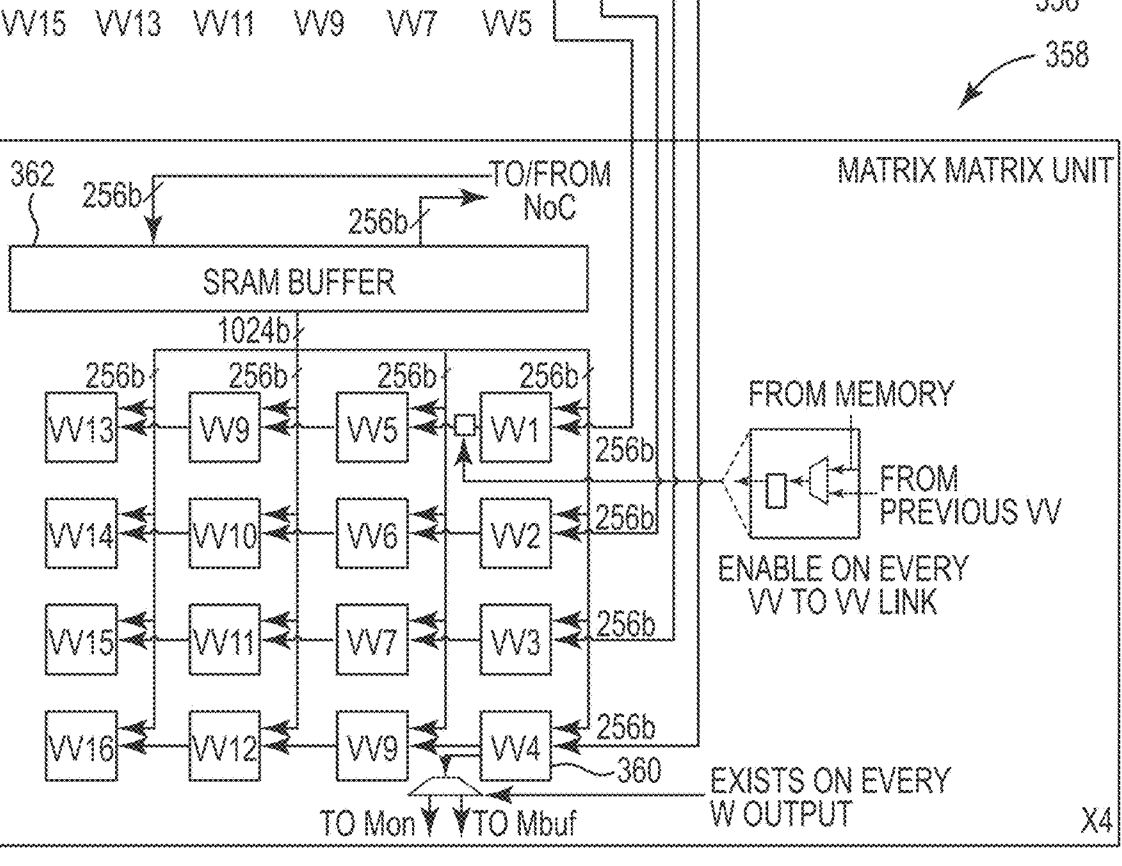
FIG. 3C is a block diagram of a second portion of the architecture illustrated in FIG. 3A.

FIG. 3A is a block diagram of an example of a memory-logic architecture in accordance with a number of embodiments of the present disclosure. FIG. 3B is a block diagram of a first portion of the architecture illustrated in FIG. 3A. FIG. 3C is a block diagram of a second portion of the architecture illustrated in FIG. 3A. The architecture includes a memory wafer 314 wafer-on-wafer bonded to a logic wafer 315. Singulated therefrom is a memory die 302 bonded to a logic die 304, in this example.

A portion of the memory die 302 is illustrated as a quantity of banks 328. In this example, there are 32 banks 328 per die 302 with a 1 gigabit per bank capacity for a total capacity for the die of 32 gigabits. Each bank 328 is divided (e.g., logically divided) into 64 sections 354, however, embodiments are not limited to this specific example. Each section has a capacity of 16 megabits. The sections 354 are arranged in rows 356.

A portion of the logic die 304 is illustrated as a quantity of clusters 352 forming a network-on-chip (e.g., a 1024-bit advanced extensible interface (AXI) network). In this example, the logic die 304 includes 32 clusters 352 (corresponding to the 32 banks of the memory die 302). However, in some embodiments, the ratio of banks to clusters is other than 1:1. In this example, there are 1024 multiply accumulators (MACs) per cluster, operating at 1.2 gigahertz. Each cluster 352 is divided into 4 matrix-matrix units 358, however, embodiments are not limited to this specific example. One matrix-matrix unit 358 is illustrated as an example.

The memory die 302 is connected to the logic die 304 across 8 buses (GBUS) 353 in this non-limiting example. Each GBUS 353 is coupled to 4 banks 328 in a column and has a bus width of 256 bits across the 4 banks 328. The bandwidth of each GBUS 353 is 32 gigabytes per second for a full-chip bandwidth of 256 gigabytes per second. The memory capacity serviced by each GBUS 353 is 4 gigabits (1 gigabit per bank 328). Any data that is transferred to the logic die 304 is available to any of the resources of the logic die 304 via the network-on-chip architecture of the logic die 304.

Data can be exchanged between each of the four rows 356 of sections 354 of the memory bank 328 and a respective matrix-matrix unit 358. In the example illustrated in FIG. 3C, the data from row 356 is provided to the matrix-matrix unit 358. The connection between each section 354 of a row 356 and the matrix-matrix unit 358 is a bus referred to as an LBUS. The width of the LBUS is 256 bits per section 354, servicing a 16-megabit memory space. The bandwidth is 32 gigabytes per second per LBUS, for a full-chip bandwidth between 4.5 and 65 terabytes per second. Each section 354 can exchange data with a respective vector-vector unit 360.

The matrix-matrix unit 358 includes 16 vector-vector units 360, which are coupled to an SRAM buffer 362 that is connected to the network-on-chip architecture of the logic die 304. Each vector-vector unit 360 is coupled to a respective memory section 354 and to one or more other vector-vector units 360. The specific quantities and connections illustrated herein are examples for explanatory purposes. One of ordinary skill in the art, having read and understood the present disclosure, could provide different quantities and arrangements of the specifically enumerated components.

Figure 4:
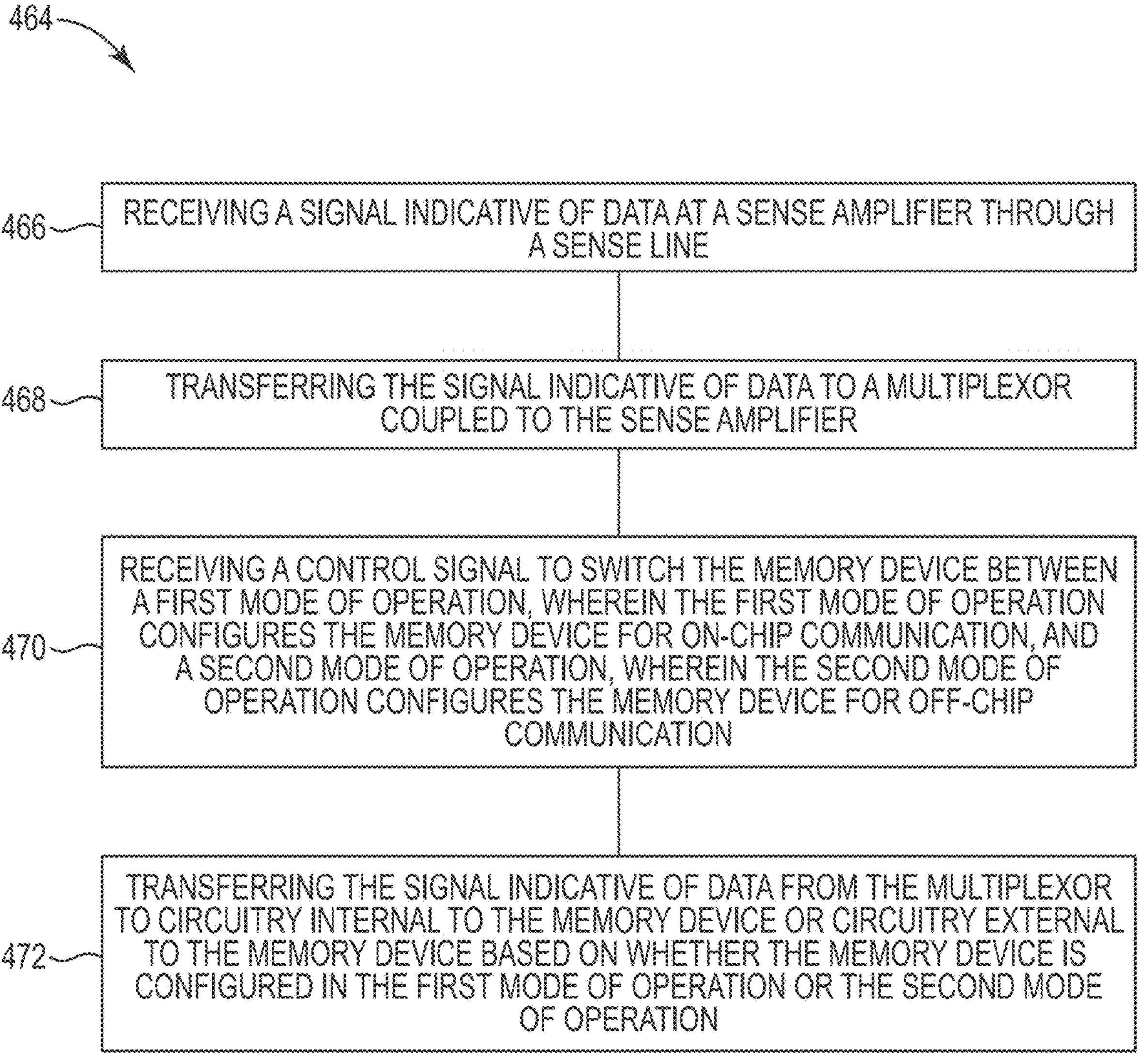
FIG. 4 is a flow diagram of an example method for operating a memory device for wafer-on-wafer formed memory and logic.

FIG. 4 is a flow diagram of an example method for operating a memory device for wafer-on-wafer formed memory and logic. Unless explicitly stated, elements of methods described herein are not constrained to a particular order or sequence. Additionally, a number of the method embodiments, or elements thereof, described herein may be performed at the same, or at substantially the same, point in time.

At block 466, the method 464 includes receiving a signal indicative of data at a sense amplifier through a sense line. The signal indicative of data can include data intended to be used in communication of data on the die or chip and/or data used in communication of data to one or more devices off the die or chip. In other words, the signal indicative of data can be transferred between memory components on a memory die or transferred between the memory die and the logic die, respectively.

At block 468, the method 464 includes transferring the signal indicative of data to a multiplexor coupled to the sense amplifier. In some embodiments, a multiplexor can receive signals indicative of data from multiple LIOs and transfer the signals indicative of data to a global I/O. In these embodiments, multiple multiplexors can each receive data indicative of data from multiple LIOs and transfer the signals indicative of data to the same global I/O.

At block 470, the method 464 includes receiving a control signal to switch the memory device between a first mode of operation, wherein the first mode of operation configures the memory device for communication of data on the die or chip, and a second mode of operation, wherein the second mode of operation configures the memory device for communication of data to one or more devices off the die or chip. At block 472, the method 464 includes transferring the signal indicative of data from the multiplexor to circuitry internal to the memory device or circuitry external to the memory device based on whether the memory device is configured in the first mode of operation or the second mode of operation. In some embodiments, the signal indicative of data can be transferred from the sense amplifier 248 to the multiplexor, a first LIO line, a second LIO line, and a global I/O line before the signal indicative of data is used in communication of data on the die or chip when the memory device is configured in the first operating mode. In some embodiments, the signal indicative of data can be transferred from the sense amplifier to a transceiver before the signal indicative of data is used in communication of data to one or more devices off the die or chip when the memory device is configured in the second mode of operation.

As used herein, "a number of" something can refer to one or more of such things. For example, a number of memory devices can refer to one or more memory devices. A "plurality" of something intends two or more.

Although specific embodiments have been illustrated and described herein, those of ordinary skill in the art will appreciate that an arrangement calculated to achieve the same results can be substituted for the specific embodiments shown. This disclosure is intended to cover adaptations or variations of various embodiments of the present disclosure. It is to be understood that the above description has been made in an illustrative fashion, and not a restrictive one. Combinations of the above embodiments, and other embodiments not specifically described herein will be apparent to those of skill in the art upon reviewing the above description. The scope of the various embodiments of the present disclosure includes other applications in which the above structures and methods are used. Therefore, the scope of various embodiments of the present disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An apparatus, comprising:

an array of memory cells configured on a memory die; and a respective transceiver associated with a respective local I/O line of the memory die, the respective transceiver configured to enable communication of data to one or more devices off the memory die, wherein:

the respective transceiver is configured to route the data to the one or more devices off the memory die through the respective local I/O line in response to receipt of a first signal from a controller; and the respective transceiver is configured to route the data to one or more devices off the memory die through a wafer-on-wafer bond in response to the respective transceiver receiving a second signal from the controller.

2. The apparatus of claim 1, wherein a respective sense amplifier of a plurality of sense amplifiers is coupled to each of a plurality of sense lines of the memory die.

3. The apparatus of claim 2, wherein the plurality of sense amplifiers is multiplexed into the respective transceiver.

4. The apparatus of claim 2, wherein the respective sense amplifier is directly coupled to circuitry outside of the memory die.

5. The apparatus of claim 4, wherein the data is transferred off-chip at a same speed at which the data leaves the respective sense amplifier and the data is transferred on-chip at a speed of a bandwidth of a global I/O line.

6. The apparatus of claim 1, wherein the respective transceiver is embedded in a column decoder.

7. The apparatus of claim 1, wherein the communication of the data on the memory die is enabled in response to the respective transceiver being in a first mode of operation.

8. The apparatus of claim 7, wherein the communication of the data on the memory die is disabled in response to the respective transceiver being in a second mode of operation.

9. An apparatus, comprising:

a plurality of tiles coupled to a global input/output (I/O) bus, wherein each tile includes a respective array of memory cells configured on a respective memory die; and a respective transceiver associated with a respective local I/O line and a wafer-on-wafer bond, wherein:

the respective transceiver is configured to enable communication of data off the respective memory die via the respective local I/O line in response to receipt of a first signal from a controller; and the respective transceiver is configured to enable communication of the data off the respective memory die via the wafer-on-wafer bond in response to receipt of a second signal from the controller.

10. The apparatus of claim 9, wherein the respective array of memory cells is coupled to sense lines and access lines of the respective memory die.

11. The apparatus of claim 9, wherein the wafer-on-wafer bond includes bond pads at the respective transceiver.

12. The apparatus of claim 11, wherein each of the bond pads is associated with a local I/O prefetch bus.

13. The apparatus of claim 11, wherein each of the bond pads is associated with a sense amplifier stripe.

14. The apparatus of claim 9, wherein the respective memory die has a same footprint as multiple logic die.

15. The apparatus of claim 14, wherein the respective memory die and the multiple logic die are singulated as a single package.

16. The apparatus of claim 9, wherein a logic die has a same footprint as multiple memory die.

17. The apparatus of claim 16, wherein the logic die and the multiple memory die are singulated as a single package.

18. The apparatus of claim 9, wherein a number of local I/O lines used in the communication of the data off of the respective memory die is greater than a number of local I/O lines used in the communication of the data on the respective memory die.

19. A method, comprising:

receiving a control signal to switch a memory device between:

a first mode of operation, wherein the first mode of operation configures the memory device for communication of data on a memory die via local input/output lines; and a second mode of operation, wherein the second mode of operation configures the memory device for communication of data to one or more devices off the memory die via a wafer-on-wafer bond; and transferring a signal indicative of data from a multiplexor configured on the memory die to circuitry internal to the memory device or circuitry external to the memory device based on whether the memory device is configured in the first mode of operation or the second mode of operation.

20. The method of claim 19, further comprising disabling the communication of the data to the one or more devices off the memory die via the wafer-on-wafer bond when the memory device is in the first mode of operation.

* * * * *